United States Patent [19]

Daluge et al.

[11] Patent Number: 5,015,647

[45] Date of Patent: May 14, 1991

[54] METHOD FOR TREATING VIRAL INFECTIONS

[75] Inventors: Susan M. Daluge; Harry J. Leighton, both of Chapel Hill; Sandra N. Lehrman, Durham, all of N.C.

[73] Assignee: Burroughs Wellcome Co., Research Triangle Park, N.C.

[21] Appl. No.: 383,248

[22] Filed: Jul. 19, 1989

Related U.S. Application Data

[63] Continuation of Ser. No. 42,423, Apr. 24, 1987, abandoned, Continuation-in-part of Ser. No. 856,582, Apr. 25, 1987.

[51] Int. Cl.$^5$ ............................................. A61K 31/52
[52] U.S. Cl. .................................................... 514/263
[58] Field of Search ......................................... 514/263

[56] References Cited

U.S. PATENT DOCUMENTS 4,593,095 6/1986 Swyder et al. ...................... 514/263
4,612,315 9/1986 Jacobson et al. ................... 514/263

Primary Examiner—Jerome D. Goldberg
Attorney, Agent, or Firm—Donald Brown

[57] ABSTRACT

The present invention relates to certain novel 8-phenylxanthines substituted in the 3 or 4 position of the phenyl group by an alkenylene, alkenyleneoxy, alkynylene or alkynyleneoxy bearing a terminal acidic grouping, and to their use in human and veterinary therapy, particularly for conditions associated with the cell surface effects of adenosine and in antiviral, especially antiretroviral, chemotherapy.

6 Claims, No Drawings

METHOD FOR TREATING VIRAL INFECTIONS

This is a continuation of application Ser. No. 07/042,423 filed on Apr. 24, 1987, now abandoned, which is a continuation-in-part of Ser. No. 06/856,582 filed on Apr. 25, 1986, now abandoned.

The present invention relates to a class of novel xanthines and salts and solvates thereof, processes and intermediates or their preparation, pharmaceutical formulations containing the, and to their use in human and veterinary medicine. The novel xanthines to which the present invention relates are of value in medical therapy on the basis of two quite distinct therapeutic effects of the compounds, first their effect an andenosine antagonists and secondly their effect as antiviral agents.

The present invention is thus concerned, at least in part, with the treatment and prophylaxis of virus infections, especially retrovirus infections, as described in more detail below.

In the comparatively new field of antiviral chemotherapy, few drugs exist which effectively combat the virus per se, owing to the difficulty of attacking the virus while leaving uninfected host cells unimpaired. It has recently been established that certain stages in the virus life-cycle, which vary form species to species, are specified by the virus itself. These stages may prove susceptible to attack where they differ sufficiently from any corresponding host-cell function. However, owing to great similarity between viral and host functions, effective treatments have proven very difficult to identify.

One group of viruses which has recently assumed a particular importance are the retroviruses. Retroviruses form a sub-group of RNA viruses which, in order to replicate, must first reverse transcribe' the RNA of their genome into DNA ('transcription' conventionally describes the synthesis of RNA from DNA). Once in the form of DNA, the viral genome is incorporated into the host cell genome, allowing it to take full advantage of the host cell's transcription/translation machinery for the purposes of replication. Once incorporated, the viral DNA is virtually indistinguishable from the host's DNA and, in this state, the virus may persist for as long as the cell lives. As it is virtually invulnerable to attack in this form, any treatment must be directed at another stage of the virus life cycle and will, of necessity, have to be continued until all virus-infected cells have died.

HTLV-I and HTLV-II are both retroviruses and are known to be causative agents of leukaemia in man. HTLV-I infections are especially widespread and are responsible for many deaths world-wide each year.

A species of retrovirus has also been reproducibly isolated from patients with Acquired Immune Deficiency Syndrome (AIDS). The virus has previously been referred to as human T-cell lymphotropic virus III (HTLV III), AIDS associated retrovirus (ARV), or lymphadenopathy associated virus (LAV),. but is known internationally as human immunodeficiency virus (HIV) (Nature, Vol 321 1st May 1986). This virus (referred to herein as HIV) has been shown preferentially to infect and destroy T-cells bearing the OKT$^4$ surface marker and is now generally accepted as the aetiologic agent of AIDS. The patient progressively loses this set of T-cells, upsetting the overall balance of the immune system, reducing his ability to combat other infections, and predisposing him to opportunistic infections which frequently prove fatal. Thus, the usual cause of death in AIDS victims is by opportunistic infection, such as pneumonia or virally induced cancers, and not as a direct result of HIV infection. Other conditions associated with HIV infection include thrombocytopaenia purpura and Kaposis sarcoma.

Recently, HIV has also been recovered from other tissue types, including B-cells expressing the T$^4$ marker, macrophages and non-blood associated tissue in the central nervous system. This infection of the central nervous system is not necessarily associated with classical AIDS and has been discovered in patients with asymptomatic HIV infections. HIV infections of the CNS is associated with progressive demyelination, leading to wasting and such symptoms as encephalopathy, progressive dysarthria, ataxia and disorientation. Peripheral neuropathy may also be associated with HIV infection. Further conditions associated with HIV infection are the asymptomatic carrier state, progressive generalised lymphadenopathy (PGL) and AIDS-related complex (ARC)

The existence of these human retroviruses and others has only recently been recognised and, as the disease with which they are linked are of a life-threatening nature, there exists an urgent need to develop ways to combat these viruses.

Various drugs have now been proposed as 'cures' for AIDS. These include antiomoniotungstate, suramin, ribavirin and isoprinosine, which are either somewhat toxic or have shown no marked anti-retroviral activity. As the AIDV genome is incorporated into the host cell DNA after infection and is virtually invulnerable to attack in this state, it will persist as long as the host cell survives, causing new infection in the meantime. Thus, any treatment of AIDS would have to be for an extended period, possibly life, requiring substances with an acceptable toxicity.

We have now discovered a novel class of xanthine compounds, described in more detail below, that possess antiviral activity, particularly against retroviruses, especially HTLV-III.

In addition to their antiviral activity, the xanthine compounds also have activity as adenosine antagonists. Theophylline, a naturally occurring alkaloid, is 1,3-dimethylxanthine and is known to antagonise the receptors for adenosine. Although its precise mechanism of action requires further clarification, it is believed that this property of theophylline accounts, at least to some extent, for its ability to stimulate the central nervous system and cardiac muscle, to act on the kidney to produce diuresis, and to relax smooth muscle, notably bronchial muscle (*Trends in Pharmacol. Sci.*, Jan 1980, 1, 129 to 132;*Life Sci.*, 1981, 28, 2083 to 2097; and The Pharmacological Basis of Therapeutics, 6th Edition, Macmillan Publishing Co, pages 592 to 607). Various derivatives of theophylline have been prepared in recent years including substituted 8-phenylxanthines that were prepared as part of a structure-activity study (*Biochem. Pharmac.*,1981, 30 325 to 333 and *Proc. Nat. Acad. Sci.*, 1983, 80, 2077 to 2080). Some of these bind to adenosine receptors with greater affinity than theophylline (European Patent Publication No. 92398).

A structurally distinct class of novel 8-phenylxanthines has now been discovered, which are characterised by the presence of an alkenyl, alkenyloxy, alkynlene or alkynyleneoxy moiety terminally substituted by an acidic grouping on the 3- or 4-position of the phenyl ring. These xanthine derivatives have been found to possess therapeutic activity in that not only are they able to antagonise effects of adenosine in tissue preparations, but they also show surprisingly good activity against viral infections. Such activity is of therapeutic value in human and veterinary medicine and in particular in the treatment or prophylaxis of AIDS and other retroviral infections and of pathophysiological disorders arising from the cell surface effects of adenosine.

Certain 8-phenylxanthines substituted by various groups on the pyrimidine and phenyl rings are described in UK Patent Application No. 2 135 311 A, reference being made to the adenosine antagonist activity of such compounds as measured by in vitro binding data only. However, the data provided in the Specification for the adenosine antagonist activity of such compounds illustrates that the binding of the compounds varies considerably according to the identity of the substituents on the pyrimidine and phenyl rings.

The xanthine compounds according to the present invention constitute a structurally distinct class of 8-phenyl xanthines, characterised by the presence on the 3- or 4- position of the phenyl ring of an unsaturated grouping terminally substituted by an acidic grouping. These compounds have been found to possess advantageous adenosine antagonist activity as demonstrated by their response to the guinea pig ileum twitch test described hereinafter and, moreover, have shown superior activity to analogous compounds described in UK Patent Application No. 2 135 311 A, as shown in heat block models in vivo (described later). As indicated above the compounds also show suprisingly good activity against viral infections. The compounds are, thus, of therapeutic value.

Accordingly, the present invention provides a compound of formula (I):

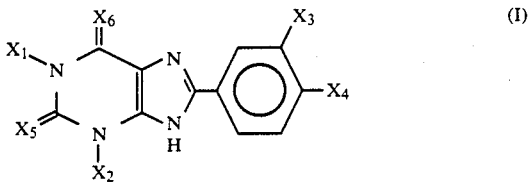

wherein
$X_1$ and $X_2$ are the same or different and are hydrogen, $C_{1-6}$ alkyl, $C_2$–alkenyl or $C_{7-12}$ aralkyl provided that both $X_1$ and $X_2$ are not hydrogen;
one of $X_3$ and $X_4$ is hydrogen, $C_{1-6}$ alkyl, trifluoromethyl, $C_{1-6}$ alkoxy, halo, nitro, amino, $C_{1-6}$ alkoxycarbonyl or carboxy and the other is a group -Y-Z where Y is $C_{2-6}$ alkenylene, or $C_{3-6}$ alkenyleneoxy, $C_{2-6}$ alkenylene or $C_{3-6}$ alkynyleneoxy and Z is carboxy, sulphonyl or phosphonyl or a $C_{1-9}$ alkyl ester, a $C_{7-12}$ aralkyl ester or a $C_{6-12}$ aryl ester thereof, or is 5-tetrazolyl; and
$X_5$ and $X_6$ are the same or different and are oxygen or sulphur; or a salt or solvate thereof.

The compounds of the invention may exist in a number of tautomeric forms and all such forms, individually and as mixtures, are embraced by the above definition of formula (I) even though only one tautomer is depicted for convenience.

A preferred sub-class of $X_1$ and $X_2$, when $C_{7-12}$ aralkyl, is benzyl.

Preferably, $X_1$ and $X_2$ are the same or different and are hydrogen or $C_{1-6}$ alkyl. In particular, $x_1$ and $X_2$ are the same or different and are both $C_{1-6}$ alkyl. Examples of $X_1$ and $X_2$, when $C_{1-6}$ alkyl, include both branched and straight chain alkyl, for example methyl, ethyl, n- and iso- propyl, and n-, iso- and tertbutyl. Preferred examples of $X_1$ and $X_2$, when $C_{1-6}$ alkyl, include ethyl, n-propyl and n-butyl, especially n-propyl.

Preferably, one of $X_3$ and $X_4$ is hydrogen.

A preferred sub-class of Y is (in straight- or branched-chain form) $C_{2-3}$ alkenylene (such as vinylene, and propenyleneoxy) or $C_{2-6}$ alkenylene (such as acetylene). Most preferably, Y is vinylene or acetylene. Preferably, Z, when a $C_{1-9}$ alkyl ester, is a $C_{1-6}$ alkyl ester. Examples of Z, when a $C_{1-6}$ alkyl ester, include the methyl and ethyl esters.

Examples of Z, when a $C_{7-12}$ aralkyl ester, include the benzyl ester.

Examples of Z, when a $C_{6-12}$ aryl ester, include the phenyl ester.

As used herein in relation to the definition of Z, a phosphonyl ester includes both the dibasic ester and the monobasic half-ester.

As used herein, 5-tetrazoyl is the group having the structural formula:

which thus embraces both tautomeric forms thereof and which are identifiable as 5-(1H)-tetrazolyl and 5-(2H)-tetrazolyl.

Included within the definition of Z is a preferred sub-class, where Z is carboxy, sulphonyl or phosphonyl or a $C_{1-6}$ alkyl ester thereof. Preferably, Z is carboxy or a $C_{1-6}$ alkyl, such as a methyl or ethyl, ester thereof.

Most preferably, $X_3$ is hydrogen and $X_4$ is the group -Y-Z where Y is vinylene and Z is carboxy.

Preferably, both $X_5$ and $X_6$ are oxygen.

Those compounds of formula (I) wherein $X_1$ and $X_2$ are the same or different and are $C_{7-12}$ aralkyl (e.g. benzyl) or $C_{3-4}$ straight chain alkyl, $X_3$ is hydrogen, $X_4$ is -Y-Z wherein Y is ethenylene good anti-retroviral activity, especially against AIDV.

The compounds of the present invention are capable of existing as geometric and optical isomers. All such isomers, individually and as mixtures, are included within the scope of the present invention. Compounds in the form of the E-geometrical isomers, are particularly preferred.

Of the compounds exemplified hereinafter, those that are preferred include
1. (E)-4-(1,2,3,6-tetrahydro-1,3-dimethyl-2,6-dioxo-9H-purin-8-yl)cinnamic aicd,
2. (E)-4-(1,2,3,6-tetrahydro-3-methyl-2,6-dioxo-1-propyl-9H-purin-8-yl)cinnamic acid.
3. (E)-4-(1,3-diethyl-1,2,3,6-tetrahydro-2,6-dioxo-9H-purin-8yl)cinnamic acid,
4. (E)-4-(1,3-diallyl-1,2,3,6-tetrahydro-2,6-dioxo-9H-purin-8-yl)cinnamic acid,
5. (E)-4-(1,2,3,6-tetrahydro-2,6-dioxo-1,3-dipropyl-9H-purin-8-yl)cinnamic acid,
6. (E)-4-(1,2,3,6-tetrahydro-3-methyl-2,6dioxo-9H-purin-8-yl)cinnamic acid,
7. (E)-4-(3-ethyl-1,2,3,6-tetrahydro-2,6-dioxo-9H-purin-8-yl)cinnamic acid,
8. (E)-4-(1,2,3,6-tetrahydro-2,6-dioxo-3-propyl-9H-purin-8-yl)cinnamic acid,
9. (E)-4-(1,2,3,6-tetrahydro-3-isobutyl-2,6-dioxo-9H-purin-8-yl)cinnamic acid,
10. (E)-4-(1,2,3,6-tetrahydro-1-methyl-2,6-dioxo-3-propyl-9H-purin-8-yl)cinnamic acid, 11. (E)-4-(1,2,3,6-tetrahydro-3-isobutyl-1-methyl-2,6-dioxo-9H-purin-8-yl)cinnamic acid,
12. (E)-4-(1-ethyl-1,2,3,6-tetrahydro-3-methyl-2,6-dioxo-9H-purin-8-yl)cinnamic acid,
13. (E)-4-(1,3-dibutyl-1,2,3,6-tetrahydro-1,6-dioxo-1,6-dioxo-9H-purin-8-yl)cinnamic acid,
14. (E)-4-(1,3-dibenzyl-1,2,3,6-tetrahydro-2,6-dioxo-9H-purin-8-yl)cinnamic acid,
15. (E)-4-(3-butyl-1,2,3,6-tetrahydro-1-methyl-2,6-dioxo-9H-purin-8-yl)cinnamic acid,
16. (E)-4-(1-butyl-1,2,3,6-tetrahydro-3-methyl-2,6-dioxo-9H-purin-8-yl)cinnamic acid,
17. (E)-4-(3-benzyl-1,2,3,6-tetrahydro-1-methyl-2,6-dioxo-9H-purin-8-yl)cinnamic acid,
18. (E)-4-(1,2,3,6-tetrahydro-1,3-diisobutyl-2,6-dioxo-9H-purin-8-yl)cinnamic acid,
19. (E)-4-(1,2,3,6-tetrahydro-1,3,-dimethyl-6-oxo-2thio-9H-purin-8-yl)cinnamic acid,
20. (E)-4-[3-(4-cyanobenzyl)-1,2,3,6-tetrahydro-1-methyl-2,6dioxo-9H-purin-8-yl]cinnamic acid,
21. (E)-4-[3-(3-cyanobenzyl)-1,2,3,6-tetrahydro-1-methyl-2,6-dioxo-9H-purin-8-yl]cinnamic acid,
22. 3-[4-(1,2,3,6-tetrahydro-2,6-dioxo-1,3dipropyl-9H-purin-8-yl)phenyl]propiolic acid,
23. (E)-4-[1-(4-cyanobenzyl)-1,2,3,6-tetrahydro-3-methyl-2,6-dioxo-9H-purin-8-yl]cinnamic aicd,
24. (E)-4-(1-benzyl-1,2,3,6-tetrahydro-2,6-dioxo-3-propyl-9H-purin-8-yl)cinnamic acid,
25. (E)-4-(3-benzyl-1,2,3,6-tetrahydro-2,6-dioxo-1-propyl-9H-purin-8-yl)cinnamic acid.
26. (E)-4-(1-benzyl-1,2,3,6-tetrahydro-2,6-dioxo-3-butyl-9H-purin-8-yl)cinnamic acid.
27. (E)-4-(3-benzyl-1,2,3,6-tetrahydro-2,6-dioxo-1-butyl-9H-purin-8-yl)cinnamic acid.

Compounds 13, 14 and 24–27 are particularly preferred on account of their antiviral activity, compound 14 having especially potent activity against AIDV.

As salts of a compound of formula (I), there are included acid addition salts of the compound, wherein one of $X_3$ and $X_4$ is amino, and salts comprising the compound, wherein one of $X_3$ and $X_4$ is carboxy, or wherein the other is a group -Y-Z where Y is as hereinbefore defined and Z is carboxy, sulphonyl or phosphonyl, as an anionic species, together with a cation. In both types of salts, the pharmacological activity resides in the moiety derived from the compound of the invention as defined herein and the identity of the other component is of less importance although for therapeutic purposes it is, preferably, pharmaceutically acceptable to the recipient of the salt. Examples of pharmaceutically acceptable acid addition salts include those derived from mineral acids, such as hydrochloric, hydrobromic, phosphoric, metaphosphoric, nitric and sulphuric acids, and organic acids, such as tartaric, acetic, citric, malic, lactic fumaric, benzoic, glycollic, gluconic, succinic and arylsulphonic, for example p-toluenesulphonic, acids. Examples of salts comprising the compound, wherein one of $X_3$ and $X_4$ is carboxy, or wherein the other is a group -Y-Z where Y is as hereinbefore defined and Z is carboxy, sulphonyl or phosphonyl, as an anionic species, together with a cation, include ammonium salts, alkali metal salts, such as sodium and potassium salts, alkaline earth salts, such as magnesium and calcium salts, and salts formed with organic bases, for example, amino salts derived from mono-, di- or tri-(lower alkyl) or (lower alkanol)amines, such as triethanolamine and diethylaminoethylamine, and salts with heterocyclic amines such as piperidine, pyridine, piperazine and morpholine. The pharmaceutically acceptable salts together with the salts which are not thus acceptable have utility in the isolation and/or the purification of the compounds of the invention, and the unacceptable salts are also useful in being convertible to the acceptable salts by techniques well known the art.

Examples of a solvate of a compound of formula (I) or a salt thereof include an hydrate, for example the monohydrate.

The compounds of the present invention and the salts and solvates thereof may be prepared by any suitable process. In this regard, the present invention provides a first process for the preparation of a compound of formula (I), as defined hereinbefore, or a salt or solvate thereof, which comprises cyclising, in the presence of an oxidant, a compound of formula (II):

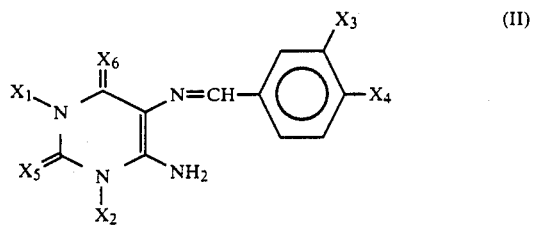

wherein $X_1$ to $X_6$ are as defined hereinbefore; optionally converting X or $X_2$, or $X_3$ or $X_4$ in the resulting compound of formula (I) into another $X_1$ or $X_2$, or $X_3$ or $X_4$ respectively; in the case where one or both of $X_5$ and $X_6$ is/are oxygen, optionally converting one or both of $X_5$ and $X_6$ into sulphur; and optionally forming a salt or solvate thereof.

The cyclisation, in the presence of an oxidant, of a compound of formula (II) may be carried out conventionally, for example, at an ambient or elevated temperature in a solvent, such as nitrobenzene.

Examples of an oxidant for use in the cyclisation of a compound of formula (II) include nitrobenzene, oxygen with or without a palladium/carbon catalyst, or ferric chloride. Of these, nitrobenzene is preferred since it can also function as the solvent in which the cyclisation may be carried out. Examples of the optional conversion of $X_1$ or $X_2$ in the resulting of formula (I) into another $X_1$ or $X_2$ respectively are generally known in the art. One useful example is the optional conversion by reduction of 4-nitrobenzyl (for $X_2$) into 4-aminobenzyl. A preferred reducing agent for such reduction is hydrogen and platinum or platinum on charcoal.

Examples of the optional conversion of $X_3$ or $X_4$ in the resulting compound of formula (I) into another $X_3$ or $X_4$ respectively are generally known in the art. One useful example is the optional conversion by hydrolysis of the group -Y-Z where Y is as hereinbefore defined and Z is a $C_{1-9}$ alkyl, a $C_{7-12}$ aralkyl or a $C_{6-12}$ aryl carboxylic ester, a $C_{1-9}$ alkyl, a $C_{7-12}$ aralkyl or a $C_{6-12}$ aryl sulphonyl ester, or a $C_{1-9}$ alkyl, a $C_{7-12}$ aralkyl or a $C_{6-12}$ aryl phosphonyl ester into the group -Y-Z where Y is as hereinbefore defined and Z is carboxy, sulphonyl or phosphonyl respectively. Such hydrolysis may be carried out conventionally, for example, by using, in the case of a carboxylic or sulphonyl ester, aqueous sodium hydroxide or, in the case of a phosphonyl ester, concentrated hydrochloric acid and glacial acetic acid.

In the case where one or both of $X_5$ and $X_6$ is/are oxygen, the optional conversion of one or both of $X_5$ and $X_6$ into sulphur may be carried out with phosphorus pentasulphide (*J. Org. Chem.*, 1977, 42, 2470).

The optional formation of a salt or solvate of a compound of formula (I) may be carried out using techniques well known in the art.

The compound of formula (II) may be prepared by reacting a compound of formula (III):

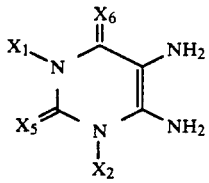
(III)

wherein $X_1$ and $X_2$ and $X_5$ and $X_6$ are as defined hereinbefore, with a compound of formula (IV):

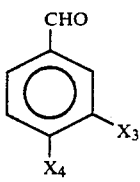
(IV)

wherein $X_3$ and $X_4$ are as defined hereinbefore.

The reaction between the compounds of formulae (III) and (IV) may be carried out conventionally, for example, by heating under reflux in a solvent, such as a mixture of acetic acid and methanol. It is, however, a preferred aspect of this process of the present invention that the resulting Schiff's base is not isolated but that the two stages leading to the compound of the present invention—the reaction between the compounds of formulae (III) and (IV) and the cyclisation of the resulting compound of formula (II)—are carried out in one operation in the same reaction vessel. In these circumstances, the reaction between the compounds of formulae (III) and (IV) is, preferably, carried out under reflux in nitrobenzene.

The compound of formula (III) may be prepared by, reducing a compound of formula (V):

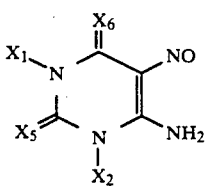
(V)

wherein $X_1$ and $X_2$ and $X_5$ and $X_6$ are as defined hereinbefore.

The reduction of the compound of formula (V) is, preferably, carried out with ammonium sulphide in the manner as described in U.S. Pat. No. 2 602 795.

The compound of formula (V) may be prepared by reacting a compound of formula (VI):

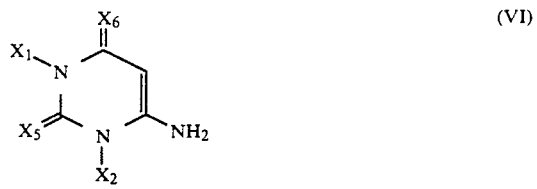
(VI)

wherein $X_1$ and $X_2$ and $X_5$ and $X_6$ are as defined hereinbefore, with nitrous acid; and optionally converting $X_1$ or $X_2$ into another $X_1$ or $X_2$ as defined herein.

The reaction between the compound of formula (VI) and nitrous acid (which may be prepared in situ from sodium nitrite and glacial acetic acid) is, preferably, carried out in accordance with the procedure described in *J. Org. Chem.*, 1951, 16, page 1879 et seq.

Examples of the optional conversion of $X_1$ or $X_2$ into another $X_1$ or $X_2$ include the optional conversion of hydrogen into $C_{1-6}$ alkyl, $C_{2-6}$ alkenyl or $C_{7-12}$ aralkyl *optionally substituted in the aryl ring by* $C_{1-6}$ alkyl, $C_{1-6}$ alkoxy, hydroxy, halo, nitro, amino or cyano. In fact, if it is desired to prepare a compound of formula (I), wherein $X_1$ is a bulkier group than $X_2$, then it is preferred first to prepare the compound of formula (VI), wherein $X_1$ is hydrogen, and then to convert the hydrogen atom into the desired group for $X_1$.

The present invention also provides a second process for the preparation of a compound of formula (I), wherein the other of $X_3$ and $X_4$ is the group -Y-Z where Y is $C_{3-6}$ alkenyleneoxy and Z is as hereinbefore defined, or a salt or solvate thereof, which comprises reacting a compound of formula (VII):

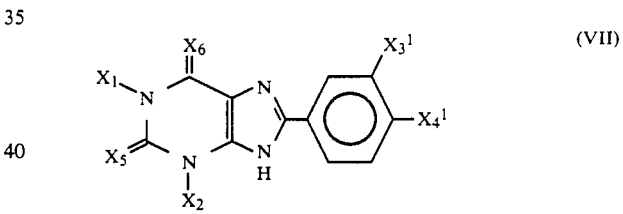
(VII)

wherein $X_1$ and $X_2$ and $X_5$ and $X_6$ are as hereinbefore defined and one of $X_3^1$ and $X_4^1$ is as defined hereinbefore for one of $X_3$ and $X_4$ and the other is hydroxy, with a compound of formula (VIII);

$$L-Y^1-Z \qquad (VIII)$$

wherein L is a leaving group, $Y^1$ is $C_{3-6}$ alkenylene and Z is as hereinbefore defined; optionally converting $X_1$ or $X_2$, or $X_3$ or $X_4$ in the resulting compound of formula (I) into another $X_1$ or $X_2$, or $X_3$ or $X_4$ respectively; in the case where one or both of $X_5$ and $X_6$ is/are oxygen, optionally converting one or both of $X_5$ and $X_6$ into sulphur; and optionally forming a salt or solvate thereof.

The reaction between the compounds of formulae (VII) and (VIII) may be carried out conventionally, for example, in the presence of a base, such as an alkali metal alkoxide, in particular potassium t-butoxide, in a solvent, such as dimethyl sulphoxide, under an inert atmosphere.

A preferred example of the leaving group (L) is bromo.

Examples of the optional conversion of $X_1$ or $X_2$ in the resulting compound of formula (I) into another $X_1$ or $X_2$ respectively are as described hereinbefore in relation to the corresponding optional conversions carried out on the compound of formula (I) resulting from the cyclisation of a compound of formula (II). Examples of the optional conversion of $X_3$ or $X_4$ in the resulting compound of formula (I) into another $X_3$ or $X_4$ respectively are generally known in the art. An example is the optional conversion by hydrolysis of the group -Y-Z where Y is $C_{3-6}$ alkenyleneoxy and Z is $C_{1-9}$ alkyl, a $C_{7-12}$ aralkyl or a $C_{6-12}$ aryl carboxylic ester, a $C_{1-9}$ alkyl, a $C_{7-12}$ aralkyl or a $C_{6-12}$ aryl sulphonyl ester or a $C_{1-9}$ alkyl, a $C_{7-12}$ aralkyl or a $C_{6-12}$ aryl phosphonyl ester into the group -YZ where Y is $C_{3-6}$ alkenyleneoxy and Z is carboxy, sulphonyl or phosphonyl. Such hydrolysis may be carried out as described hereinbefore.

In the case where one or both of $X_5$ and $X_6$ is/are oxygen, the optional conversion of one or both of $X_5$ and $X_6$ into sulphur may be carried out as described hereinbefore.

The optional formation of a salt or solvate of a compound of formula (I) may be carried out using techniques well known in the art.

It should be noted that, during the reaction between the compounds of formulae (VII) and (VIII), a side-reaction may occur at the nitrogen atom in the 7-position in the compound of formula (VII). It will, therefore, be appreciated that the reagents and conditions should be chosen so as to minimise the occurrence of any such side-reaction. In any case, it is preferred, for reasons of a better yield and a cleaner product, that the preparation of a compound of formula (I), wherein the other of $X_3$ and $X_4$ is the group -Y-Z where Y is $C_{3-6}$ alkenyleneoxy and Z is as hereinbefore defined, is carried out using the first process of the invention involving the cyclisation of a compound of formula (II).

The compound of formula (VII) may be prepared by reacting a compound of formula (III), as defined hereinbefore, with a compound of formula (IX):

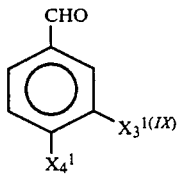 (IX)

wherein $X_3^1$ and $X_4^1$ are as hereinbefore defined.

The reaction between the compounds of formulae (III) and (IX) may be carried out analogously to the reaction between the compounds of formulae (III) and (IV) as described hereinbefore.

The present invention also provides a third process for the preparation of a compound of formula (I), as defined hereinbefore, or a salt or solvate thereof, which comprises cyclising a compound of formula (X):

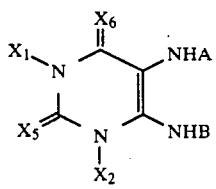 (X)

wherein $X_1$ and $X_2$ and $X_5$ and $X_6$ are as defined hereinbefore and one of A and B is hydrogen and the other is 3-($X_3$)-4-($X_4$)-benzoyl in which $X_3$ and $X_4$ are as defined hereinbefore; optionally converting $X_1$ or $x_2$, or $X_3$ or $X_4$ in the resulting compound of formula (I) into another $X_1$ or $X_2$, or $X_3$ or $X_4$ respectively; in the case where one or both of $X_5$ and $X_6$ is/are oxygen, optionally converting one or both of $X_5$ and $X_6$ into sulpur; and optionally forming a salt or solvate thereof.

The cyclisation of a compound of formula (X) may be carried out conventionally. For example, in the case where B is hydrogen and A is 3-($X_3$)-4-($X_4$)-benzoyl, the cyclisation is, preferably, carried out in the presence of aqueous base, such as aqueous sodium hydroxide, at elevated temperature, and, in the case where A is hydrogen and B is 3-($X_3$)-4-($X_4$)-benzoyl, the cyclisation usually proceeds spontaneously in view of the highly nucleophilic 5-amino substituent.

Examples of the optional conversion of $X_1$ or $X_2$, or $X_3$ or $X_4$ in the resulting compound of formula (I) into another $X_1$ or $X_2$, or $X_3$ or $X_4$ respectively are as described hereinbefore in relation to the corresponding optional conversions carried out on the compound of formula (I) resulting from the cyclisation of a compound of formula (II).

In the case where one or both of $X_5$ and $X_6$ is/are oxygen, the optional conversion of one or both of $X_5$ and $X_6$ into sulphur may be carried out as described hereinbefore.

The optional formation of a salt or solvate of a compound of formula (I) may be carried out as described hereinbefore. In this regard, it should be noted that, if the cyclisation of a compound of formula (X) is carried out in the presence of aqueous base, then the compound of formula (I) is normally obtained as the salt. The free acid of formula (I) can be regenerated simply by treatment of the salt with acid.

The compound of formula (X), wherein B is hydrogen and A is 3-($X_3$)-4-($X_4$)-benzoyl, may be prepared by reacting a compound of formula (III), as defined hereinbefore, with a compound of formula (XI):

 (XI)

wherein $X_3$ and $X_4$ are as defined hereinbefore and $X_7$ is hydroxy, chloro, broma or $C_{1-6}$ alkylcarbonyloxy.

The reaction between the compounds of formulae (III) and (XI) may be carried out conventionally. For example, in the case where $X_7$ is hydroxy, the reaction may be carried out in the presence of a condensation promoting agent, such as dicyclohexylcarbodiimide.

The compound of formula (X), wherein A is hydrogen and B is 3-($X_3$)-4-($X_4$)-benzoyl, may be prepared by reducing a compound of formula (XII):

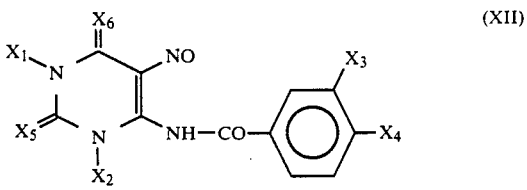 (XII)

wherein $X_1$ to $X_6$ are as hereinbefore defined.

The reduction of a compound of formula (XII) may be carried out conventionally, for example, by catalytic hydrogenation with Raney nickel or platinum or by using ammonia sulphide as described in U.S. Pat. No. 2,602,795. As mentioned previously, the 5-amino substituent of the resulting compound of formula (X), wherein A is hydrogen and B is 3-($X_3$)-4-($X_4$)-benzoyl, is highly nucleophilic with the result that the compound of formula (X) normally proceeds spontaneously to the desired compound of formula (I).

The compound of formula (XII) may be prepared by reacting a compound of formula (V), as defined hereinbefore, with a compound of formula (XI), as defined hereinbefore.

The reaction between the compounds of formulae (V) and (XI) may be carried out analogously to the reaction between the compounds of formulae (III) and (XI) described hereinbefore.

It should be noted that, if, in the reactions between the compounds of formulae (III) and (XI) and of formulae (V) and (XI), the other of $X_3$ and $X_4$ in formula (XI) is the group -Y-Z where Y is as defined hereinbefore and Z is carboxy, sulphonyl or phosphonyl, then the reagents and conditions should be chosen so as to minimise the occurrence of any competing side-reaction at the acidic group for Z and to maximise the desired reaction between the carboxy group or derivative thereof ($COX_7$) depicted in formula (XI) and the amino substituent in the 5-position in the compound of formula (III). Alternatively, the acidic group for Z may be blocked during the course of the reaction and then deblocked after its completion. Examples of preferred blocked acidic groups include $C_{1-9}$ alkyl esters, $C_{7-12}$ aralkyl esters or $C_{6-12}$ aryl esters, the blocking groups of which may be added to and removed from the acidic group in conventional manner. Because of the need to avoid a competing side-reaction either by the employment of particular reagents and conditions or by using a blocked acidic group, this process of the invention is generally the least preferred.

The compounds of formulae (II), (X) and (XII) and a number of the compounds of formulae (III), (V) and (VII), as described hereinafter, are novel intermediates of use in the preparation of the compounds of formula (I) and, thus, represent part of the present invention.

The compounds of formulae (III) and (V) that are novel intermediates are of formulae (III)[1] and (V)[1]:

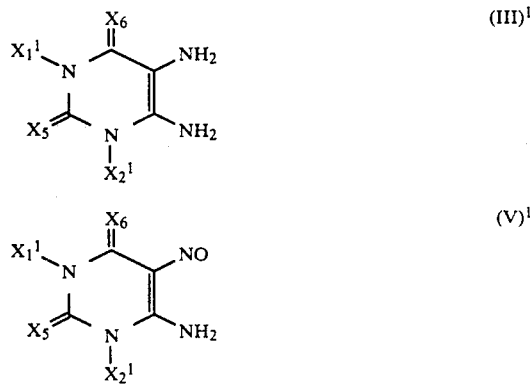

wherein $X_1^1$ is methyl and $X_2^1$ is propyl, $X_1^1$ is propyl and $X_2^1$ is methyl, $X_1^1$ is n-butyl and $X_2^1$ is methyl, $X_1^1$ and $X_2^1$ are both iso-butyl, $X_1^1$ and $X_2^1$ are both allyl, or $X_1^1$ and $X_2^1$ are the same or different and are $C_{7-12}$ aralkyl optionally substituted in the aryl ring by $C_{1-6}$ alkyl, $C_{1-6}$ alkoxy, hydroxy, halo, nitro, amino or cyano.

The compounds of formula (VII) that are novel intermediates are of formula (VII)[1]:

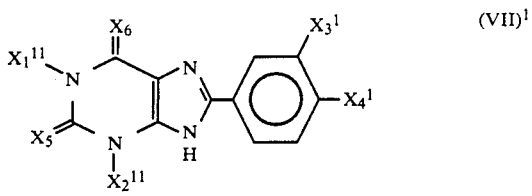

wherein $X_1^{11}$ and $X_2^{11}$ are the same or different and are hydrogen, $C_{2-6}$ alkyl, $C_{2-6}$ alkenyl or $C_{7-12}$ aralkyl optionally substituted in the aryl ring by $C_{1-6}$ alkyl, $C_{1-6}$ alkoxy, hydroxy, halo, nitro, amino or carboxy, and $X_3^1$ and $X_4^1$ are as defined hereinbefore.

The compounds of formulae (IV), (VI), (VIII), (IX) and (XI) are commercially available, or may be obtained by carrying out a published process for their preparation, or by carrying out a process analogous to a published process for the preparation of structurally analogous compounds. For example, the compounds of formula (IV), wherein the other of $X_3$ and $X_4$ is the group -Y-Z where Y is $C_{3-6}$ alkenyleneoxy and Z is as hereinbefore defined, may be obtained by alkenylating in a conventional manner the corresponding hydroxybenzaldehyde.

While it is possible for the compounds of the present invention and the salts and solvates thereof to be administered as the raw chemical, it is preferred to present them in the form of a pharmaceutical formulation. Accordingly, the present invention further provides a pharmaceutical formulation, for human or veterinary application, which comprises a compound of the present invention, or a pharmaceutically acceptable salt or solvate thereof, and a pharmaceutically acceptable carrier therefor.

The compounds according to the invention may be employed alone or in conjunction with one or more other therapeutic agents for example other anti-HIV agents e.g. 3'-azidoneucleosides such as 3'-azido-3'-deoxythymidine 2',3'-dideoxynucleosides such as 2', 3'-dideoxyadenosine or 2',3'-dideoxycytidine, immunomodulators or similar agents such as interleukin-11, interferon, granulocyte macrophage colony stimulating factor, as well as agents that may be of value for the treatment of opportunistic infections such as acyclovir, ganiciclovir, desiclovir, idoxuridine (IUDR) or trifluridine.

The expression "pharmaceutically acceptable" as used herein in relation to the carrier is used in the sense of being compatible with the compound of the present invention, or a pharmaceutically acceptable salt or solvate thereof, employed in the formulation and with any other therapeutic agent that may be present, and not being detrimental to the recipient thereof. The carrier itself may constitute one or more excipients conventionally used in the art of pharmacy that enable the compound of the present invention, or a pharmaceutically acceptable salt or solvate thereof, and any other therapeutic agent that may be present, to be formulated as a pharmaceutical formulation. The pharmaceutical formulations of the present invention include those suitable for oral, parenteral (including subcutaneous, intradermal, intramuscular and intravenous) and rectal administration although the most suitable route will probably depend upon, for example, the precise nature and severity of the condition and the identity of the recipient. The formulations may conveniently be presented in unit dosage form and may be prepared by any of the methods well known in the art of pharmacy. All methods include the step of bringing into association the active ingredient, i.e. the compound of the present invention, or a pharmaceutically acceptable salt or solvate thereof, with the carrier. In general the formulations are prepared by uniformly and intimately bringing into association the active ingredient with, a liquid carrier or, a finely divided solid carrier or both, and then, if necessary, forming the associated mixture into the desired formulation.

the pharmaceutical formulations of the present invention suitable for oral administration may be presented as discrete units, such as a capsule, cachet tablet, or lozenge, each containing a predetermined amount of the active ingredient; as a powder or granules; as a solution or a suspension in an aqueous liquid or a non-aqueous liquid such as a syrup, elixir or a draught; or as an oil-in-water liquid emulsion or a water-in-oil liquid emulsion. The formulation may also be a bolus, electuary or paste. Capsules and tablets are preferably enteric-coated.

Generally, a tablet is the most convenient pharmaceutical formulation suitable for oral administration. A tablet may be made by compressing or moulding the tablets may be prepared by compressing in a suitable machine the active ingredient in a free-flowing form, such as a powder or granules, in admixture with, for example, a binding agent, an inert diluent, a lubricating agent, a disintegrating agent and/or a surface active agent. Moulded tablets may be prepared by moulding in a suitable machine a mixture of the powdered active ingredient moistened with an inert liquid diluent. The tablets may optionally be coated or scored and may be formulated so as to provide slow or controlled release of the active ingredient.

The pharmaceutical formulations of the present invention suitable for parenteral administration include aqueous and non-aqueous sterile injection solutions which may contain, for example, an anti-oxidant, a buffer, a bacteriostat and a solute which renders the composition isotonic with the blood of the recipient, and aqueous and non-aqueous sterile suspensions which may contain, for example, a suspending agent and a thickening agent. The formulations may be presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions may be prepared from sterile powders, granules and tablets of the kind previously described.

The pharmaceutical formulations of the present invention suitable for rectal administration may be presented as a suppository containing, for example, cocoa butter and polyethylene glycol.

An advantage of the compounds of the present invention and the pharmaceutically acceptable salts and solvates thereof is that they are generally water soluble and that, they are suitable for formulation as aqueous solutions. In contrast, a number of the various substituted 8-phenylxanthines of the prior art (*Biochem. Phamac.*, 1981, 30, 325 to 353; and *Proc. Nat. Acad. Sci.*, 1983, 80, 2077 to 2080) are not soluble in water or at least not sufficiently soluble so as to permit their formulation in this way.

As mentioned hereinbefore, the compounds of the present invention and the pharmaceutically acceptable salts and solvates thereof are of use in human and veterinary medicine and in particular int he treatment or prophylaxis of AIDS and other retroviral infections and of pathophysiological disorders arising from the cell surface effects of adenosine. Accordingly, the present invention yet further provides a method for the treatment or prophylaxis of an animal with a pathophysiological disorder arising from the cell surface effects of adenosine, which comprises administering to the animal a therapeutically or prophylactically effective amount of a compound of the present invention, or a pharmaceutically acceptable salt or solvate thereof. In the alternative, there is also provided a compound of the present invention, or a pharmaceutically acceptable salt or solvate thereof, for use in human or veterinary medicine and in particular for use in the treatment or prophylaxis of pathophysiological disorders arising from the cell surface effects of adenosine.

In addition to the above, the invention provides a method for the treatment or prophylaxis of a human or non-human animal virus, especially retrovirus infection, including AIDS, which comprises administering to the human or non-human animal an effective amount of a compound according to the invention. The invention also provides a compound according to the present invention for use in the treatment or prophylaxis of such infections. The present invention further provides the use of a compound according to the invention in the manufacture of a medicament for the treatment or prophylaxis of a viral or retroviral infection, especially AIDS.

There are at least four clinical manifestations of AIDV infection, all of which are suitable for treatment or prophylaxis according to the present invention. In the initial 'carrier' state, the only indication of infection is the presence of anti-AIDV antibodies in the bloodstream. It is believed that such 'carriers' are capable of passing on the infection, e.g. by blood transfusion, sexual intercourse or used syringe needles. The carrier state may often never progress to the second stage characterised by persistant generalised lymphadenopathy (PGL). It is currently estimated that about 20% of PGL patients progress to a more advanced condition known as 'AIDS related complex' (ARC). Physical symptoms associated with ARC may include general malaise, increased temperature and chronic infections. This condition usually progresses to the final, fatal AIDS condition, when the patient completely loses the ability to fight infection.

Examples of other human retroviral infections include those caused by HTLV-I and HTLV-II (eg. HTLV-1-positive leukaemia and lymphoma). Examples of non-human animal retroviral infections include feline leukaemia virus, equine infectious anaemia virus, caprine arthritis virus, visna virus, maedi virus and other lentivirus infections. Examples of clinical conditions associated with HIV and other retrovirus infections which may be treated or prevented in accordance with the present invention include AIDS, AIDS-related couplex (ARC), progressive generalized lymphadenopathy (PGL), as well as chronic neurological conditions associated with retroviruses such as multiple sclerosis, tropical spastic paraparesis. Subjects having anti-HIV antibodies or serum HIV antigens can also be treated in accordance with the invention.

The pathophysiological disorders caused by adenosine/cell-surface interactions and requiring treatment or prophylaxis in accordance with the present invention generally arise within the cardiovascular, gastrointestinal or neuroendocrine systems since adenosine has a particularly pronounced effect on the cell surface receptors in these systems and hence on their physiology. Particular examples of such pathophysiological disorders include heart block induced by various diagnostic procedures, such as scintography, or occurring as a result of a myocardial infarct where there is increased leakage of endogenous adenosine into the extracellular environment surrounding the heart muscle (Cir. Res., 1982, 51, 569 et seq). Other examples of such conditions include asthma and irritable bowel syndrome.

The animal requiring treatment or prophylaxis with a compound of the present invention, or a pharmaceutically acceptable salt or solvate thereof, is usually a human or non-human mammal.

The route by which the compound of the present invention, or a pharmaceutically acceptable salt or solvate thereof, is administered to the animal may be oral, parenteral (including subcutaneous, intradermal, intramuscular, intravenous or rectal. If the compound of the present invention, or a pharmaceutically acceptable salt or solvate thereof, is presented in the form of a pharmaceutical formulation, which, as mentioned hereinbefore, is preferred, then the actual formulation employed will of course depend on the route of administration elected by the physician or veterinarian. For example, if oral administration is preferred, then the pharmaceutical formulation employed is, preferably, one which is suitable for such a route.

A therapeutically or prophylactically effective amount of a compound of the present invention, or a pharmaceutically acceptable salt or solvate thereof, will depend upon a number of factors including, for example, the age and weight of the animal, the precise condition requiring treatment or prophylaxis and its severity, and the route of administration, and will ultimately be at the discretion of the attendant physician or veterinarian. However, an effective amount of a compound of the present invention for the treatment or prophylaxis of pathophysiological disorders arising from the cell surface effects of adenosine, will generally be in the range of 0.1 to 50 mg/kg body weight of recipient per day, more usually in the range of 0.5 to 10 mg/kg body weight per day and most often in the range of 1 to 5 mg/kg body weight per day. Thus, for a 70 kg adult patient, the actual amount per day would most often be from 70 to 350 mg and this amount may be given in a single dose per day or more usually in a number (such as two, three or four) of sub-doses per day such that the total daily dose is the same.

An effective amount of a compound of the present invention for the treatment or prophylaxis of a virus infection will generally be in the range of 3.0 to 200 mg per kilogram body weight of the patient per day, preferably in the range of 6 to 150 mg per kilogram body weight per day and most preferably in the range 15 to 100 mg per kilogram body weight per day. The desired dose is preferably presented as two, three four, five, six or more sub-doses administered at appropriate intervals throughout the day. These sub-doses may be administered in unit dosage forms, for example, containing 10 to 2000 mg, preferably 20 to 1500 mg, and most preferably 500 to 1000 mg of active ingredient per unit dosage form.

An effective amount of a pharmaceutically acceptable salt or solvate of a compound of the present invention may be determined as a proportion of the effective amount of the compound per se.

The compounds of the present invention and the salts and solvates thereof may also be used, in a manner known generally in the art, int he isolation and purification of adenosine receptors.

The following examples and pharmacological data are provided in illustration of the present invention and should not be construed as in any way constituting a limitation thereof.

EXAMPLE 1

Preparation of
(E)-4-(1,2,3,6-tetrahydro-1,3-dimethyl-2,6-dioxo-9H-purin-8-yl)cinnamic acid 5,6-Diamino-1,3-dimethyluracil hydrate (1.70 g, 10.0 mmol) and 4-formylcinnamic acid (1.76 g, 10.0 mmol) were refluxed in acetic acid (10 mL)-methanol (100 mL) for 0.5 hour. (F)-4-[(6-Amino-1,2,3-4-tetrahydro-1,3-dimethyl-2,4-dioxo-5-pyrimidinyl)iminomethyl]cinnamic acid was precipitated as yellow powder (1.84 g, 56%); mp 299°–301° C. with effervescence.

Analysis for ($C_{16}H_{16}N_4O_4$): C, 58.53; H, 4.91; N, 17.07. Found: C, 58.36; H, 4.93; N, 16.90. Structure confirmed by $^1$H-NMMR and FI mass spectrum.

(E)-4-[(6-Amino-1,2,3,4-tetrahydro-1,3-dimethyl-2,4-dioxo-5-pyrimidinylmethyl)cinnamic acid (500 mg, 1.52 mmol) was refluxed in nitrobenzene (125 mL) for 2.5 hours with slow distillation to remove water formed. The reaction mixture was cooled and the precipitate washed with ether. Recrystallization from N,N-dimethylformamide-water gave the monohydrate of the title compound as a pale yellow powder; mp > 380° C.

Analysis for ($C_{16}H_{14}N_4O_4.H_2O$): C, 55.81; H, 4.68; N, 16.27. Found: C, 56.05: H, 4.69; N, 16.27. Structure confirmed by $^1$H-NMR and EI mass spectrum.

EXAMPLE 2:

Preparation of
(E)-4-(1,2,3,6-tetrahydro-1,3-dimethyl-2,6-dioxo-9H-purin-8-yl)cinnamic acid 5,6-Diamino-1,3-dimethyluracil hydrate (5.11 g. 30.0 mmol) and 4-formylcinnamic acid (5.29 g, 30.0 mmol) were refluxed in nitrobenzene (500 mL). The nitrobenzene was allowed to distill slowly with water formed. Fresh nitrobenzene was added to keep the volume constant. After 5 hours of reflux, the mixture was cooled and the precipitate collected (8.07 g). Recrystallization from N,N-dimethylformamide-water gave the monohydrate of the title compound as a pale yellow powder, identical with that of Example 1 by $^1$H-NMR and elemental analysis.

EXAMPLE

Preparation of
(E)-4-(1,2,3,6-tetrahydro-3-methyl-2,6-dioxo-1-propyl-9H-purin-8-yl)cinnamic acid 6-Amino-1-methyl-3-propyl-2,4(1H,3H)pyrimidinedione (V. Papesch and F. F. Schroeder, J.Org.Chem. 1951, 16 1879) (5.53 g, 27.5 mmol) was dissolved in hot 95% ethanol (20 ml)-water (120 ml). Sodium nitrite (2.32 g) and glacial acetic acid (2.4 ml) were added. The resulting mixture was allowed to cool to room temperature. Orange-pink crystals were filtered off and dried at 50° C. under vacuum to give purple crystals of 6-amino-1-methyl-5-nitroso-3-propyl-2,4 (1H,3H)-pyrimidinedione (2.92 g, 80%); mp 250°dec.

Analysis for ($C_8H_{12}N_4O_3$): C,45.28; H,5.70;N,26.40. Found: C,45.12; H,5.74; N,26.34.

5,6-Diamino-1-methyl-3-propyl-2,4(1H,3Hpyrimidinedione was prepared freshly from 6-amino-1-methyl-5-nitroso-3-propyl-2,4(1H,3H)pyrimidinedione by ammonium sulfide reduction using the method of V. Papesch, M. Grove, and F. F. Schroeder (U.S. Pat. No. 2,602,795). This diamine (2.00 g, 10.0 mmol) was condensed with 4-formylcinnamic acid (1.76g, 10.0 mmol) by the procedure of Example 2 to give the title compound as an ivory powder, after crystallization from N,N-dimethylformamide-water; mp>300° C.

Analysis for ($C_{18}H_{18}N_4O_4.1/5$ DMF): C,60.54; H,5.30; N,15.94. Found: C,60.52; H,5.22; N,16.03.

EXAMPLE 4

Preparation of (E)-4-(1,3-diethyl-1,2,3,6-tetrahydro-2,6-dioxo-9H-purin-8-yl)cinnamic acid Following an analogous procedure to that of Example 3, the title compound was prepared with a melting point greater than 360° C.

Analysis for ($C_{18}H_{18}N_4O_4$): C,61.1; H,5.12; N,15.81. Found: C,61.04; H,5.15; N,15.81.

EXAMPLE 5

Preparation of (E)-4-(1,3-diallyl-1,2,3,6-tetrahydro-2,6-dioxo-9H-purin-8-yl)cinnamic acid Following an analogous procedure to that of Example 3, the title compound was prepared with a melting point of greater than 300° C.

Analysis for ($C_{20}H_{18}N_4O_4$): C,63.48; H,4.80: N,14.81. Found: C,63,26; H,4.86; N,14.71.

EXAMPLE 6

Preparation of (E)-4-(1,2,3,6-tetrahydro-2,6-dioxo-1,3-dipropyl-9H-purin-8-yl)cinnamic acid Following an analogous procedure to that of Example 3, the title compound was prepared with a melting point of 355° C. (dec.).

Analysis for ($C_{20}H_{22}N_4O_4$): C,62.82; H,5.80; N,14.65. Found: C,62.91; H,5.84;N,14.63.

EXAMPLE 7

Preparation of (E)-4-(1,2,3,6-tetrahydro-3-methyl-2,6-dioxo-9H-purin-8-yl)cinnamic acid Following an analogous procedure to that of Example 3, the title compound was prepared with a melting point of 300° C.

Analysis for ($C_{25}H_{12}N_4O_4$): C,57.69; H,3.87;N,17.94. Found: C,57.47; H,3.90;N,17.87.

EXAMPLE 8:

Preparation of (E)-4-(3-ethyl-1,2,3,6-tetrahydro-2,6-dioxo-9H-purin-8-yl)cinnamic acid Following an analogous procedure to that of Example 3, the title compound was prepared with a melting point greater than 300° C.

Analysis for ($C_{16}H_{14}N_4O_4$): C,58.89; H,4.32; N,17.17. Found: C,58.64; H,4.36; N,17.24.

EXAMPLE 9:

Preparation of (E)-4-(1,2,3,6-tetrahydro-2,6-dioxo-3-propyl-9H-purin-8-yl)cinnamic acid Following an analogous procedure to that of Example 3, the title compound was prepared with a melting point greater than 300° C.

Analysis for ($C_{17}H_{16}N_4O_4$): C,59.94; H,4.74;N,16.46. Found: C,59.78; H,4.76; N,16.41.

EXAMPLE 10

Preparation of (E)-4-(1,2,3,6-tetrahydro-3-isobutyl-2,6-dioxo-9H-purin-8-yl)cinnamic acid Following an analogous procedure to that of Example 3, the title compound was prepared with a melting point greater than 300° C.

Analysis for ($C_{18}H_{18}N_4O_4$): C,61.01; H,5.12; N,15.81. Found: C,60.85; H,5.17; N,15.74.

EXAMPLE 11

Preparation of (E)-4-(1,2,3,6-tetrahydro-1-methyl-2,6-dioxo-3-propyl-9H-purin-8-yl)cinnamic acid Following an analogous procedure to that of Example 3, the title compound was prepared with a melting point greater than 300° C.

Analysis for ($C_{18}H_{18}N_4O_4$): C,61.01; H,5.12; N,15.81. Found: C,60,86; H,5.16; N,15.76.

EXAMPLE 12:

Preparation of (E)-4-(1,2,3,6-tetrahydro-3-isobutyl-1-methyl-2,6-dioxo-9H-purin-8-yl)cinnamic acid Following an analogous procedure to that of Example 3, the title compound was prepared with a melting point greater than 300° C.

Analysis for ($C_{19}H_{20}N_4O_4$): C,61.95; H, 5.47; N,15.21. Found: C,61.99; H,5.51; N,15.19.

EXAMPLE 13:

Preparation of (E)-4-(1-ethyl-1,2,3,6-tetrahydro-3-methyl-2,6-dioxo-9H-purin-8-yl)cinnamic acid Following an analogous procedure to that of Example 3, the title compound was prepared with a melting point greater than 300° C.

Analysis for ($C_{17}H_{16}N_4O_4$): C,60.00;H,4.74; N,16.46. Found: C,59.91; H,4.77; N,16.43.

EXAMPLE 14

Preparation of
(E)-4-(1,3-dibutyl-1,2,3,6-tetrahydro-2,6-dioxo-9H-purin-8-yl)cinnamic acid Following an analogous procedure to that of Example 3, the title compound was prepared with a melting point of 350°–355° C.

Analysis for ($C_{22}H_{26}N_4O_4$): C, 64,38; H,6.39; N, 13,65. Found: C, 64.11; H,6.42; N,13.57.

EXAMPLE 15

Preparation of
(E)-4-(1,3-dibenzyl-1,2,3,6-tetrahydro-2,6-dioxo-9H-purin-8yl) cinnamic acid Following an analogous procedure to that of Example 3, the title compound was prepared with a melting point greater than 300° C.

Analysis for ($C_{28}H_{22}N_4O_4$): C,70.28;H,4.65; N,11.71. Found: C, 70.04; H,4.67; N,11.63.

EXAMPLE 16

Preparation of
(E)-4-(3-butyl-1,2,3,6-tetrahydro-1-methyl-2,6-dioxo-9H-purin-8yl) cinnamic acid Following an analogous procedure to that of Example 3, the title compound was prepared with a melting point greater than 300° C.

Analysis for ($C_{19}H_{20}N_4O_4$): C,61.94; H,5.47; N,15.21. Found: C,61.77; H, 5.52; N,15.16.

EXAMPLE 17

Preparation of
(E)-4-(1-butyl-1,2,3,6-tetrahydro-3-methyl-2,6-dioxo-9H-purin-8-yl) cinnamic acid Following an analogous procedure to that of Example 3, the title compound was prepared with a melting point greater than 300° C.

Analysis for ($C_{19}H_{20}N_4O_4$): C,61.94; H,5.47; N,15.21. Found: C,61.70; H,5.50; N,15.11.

EXAMPLE 18

Preparation of
(E)-4-(3-benzyl-1,2,3,6-tetrahydro-1-methyl-2,6-dioxo-9H-purin-8yl) cinnamic acid.

Following an analogous procedure to that of Example 3, the title compound was prepared with a melting point greater than 300° C.

Analysis for ($C_{22}H_{18}N_4O_4$): C,65.66; H,4.51; N,13.92. Found: C,65.43; H,4.60; N,13.87.

EXAMPLE 19

Preparation of
(E)-4-(1,2,3,6-tetrahydro-1,3-diisobutyl-2,6-dioxo-9H-purin-8-yl)cinnamic acid Following an analogous procedure to that of Example 3, the title compound was prepared with a melting point greater than 300° C.

Analysis for ($C_{22}H_{26}N_4O_4$): C,64,37; H, 6.39; N,13.65. Found; C,64.23; H,6.42; N, 13.64.

EXAMPLE 20

Preparation of
(E)-4-(1,2,3,6-tetrahydro-1,3-dimethyl-6-oxo-2-thio-9H-purin-8-yl)cinnamic acid 5,6-Diamino-1,3-dimethyl-2-thiouracil (K. R. H. Woolridge and R. Slack, *J. Chem. Soc.*, 1962, 1863) (0.93 g, 5.0 mmol) and 4-formylcinnamic acid (0.88 g, 5.0 mmol) were refluxed in nitrobenzene (100 mL) for 30 minutes with slow distillation of water formed. After cooling, the yellow solid was filtered and washed, first with ethanol then with ether, to give the title compound, m.p.>320° C.

Analysis for ($C_{16}H_{14}N_4O_3S$): C,56.13; H,4.12; N, 16.35; S, 9.36. Found: C,56.21; H,4.15; N, 16.35; S, 9.44.

EXAMPLE 21:

3-[4-(1,2,3,6-tetrahydro-2,6-dioxo-1,3-dipropyl-9H-purin -8-yl) phenyl]Propiolic acid.

A suspension of (E)-4-(1,2,3,6-tetrahydro-2,6-dioxo-1,3-dipropyl-9H-purin -8-yl)cinnamic acid (4.00 g, 10.4 mmol) (Example 6) and concentrated sulfuric acid (1 ml) in absolute ethanol (1.5 L) was refluxed for 2 hours with slow distillation of 75 ml of vapor. Reflux was continued for 3 days with exclusion of moisture with 50 ml distillate being removed during the final 4 hours. the cooled suspension was filtered to yield ethyl (F)-4-(1,2,3,6-tetrahydro-2,6-dioxo-1,3-dipropyl-9Hpurin-8-yl)cinnamate as a pale yellow solid. mp>300° C.

Analysis for ($C_{22}H_{26}N_4O_4$). C,64.38; H, 6.38; N, 13.65. Found: C, 64.34; H, 6.43; N, 13.63.

A solution of bromine (1.2 g, 7.5 mmol) in glacial acetic acid (25 ml) was added over 30 minutes to a suspension of the above ethyl ester (3.00 g, 7.31 mmol) in glacial acetic acid (125 ml) at 40° C. After stirring at room temperature overnight, the suspension was treated with bromine (0.2 ml) in glacial acetic acid (25 ml), warmed at 60° C. for 3 hours, and finally treated with bromine (one drop). After cooling to room temperature, a small amount of solid was filtered off, and the filtrate was evaporated to dryness. The residue was triturated in 1:1 ethyl acetate ether (140 ml) and filtered to yield ethyl 2,3-dibromo-3-[4-(1,2,3,6-tetrahydro-2,6-dioxo-1,3-dipropyl-1H-purin-8-yl)phenyl]propionate as a pale yellow solid; m.p. 221.5°–223° C. with effervesence.

Analysis for ($C_{22}H_{26}Br_2N_4O_4$): c, 46.33; H, 4.60; N, 9.82; Br, 28.02. Found: C, 46.43; H, 4.65; N, 9.77; Br, 27.97.

A suspension of the above dibromopropionate (3.00 g, 5.26 mmol) in an anhydrous ethanolic solution (150 ml) of potassium hydroxide (1.5 g, 26 mmol) was refluxed for 21 hours, then diluted over 3 hours with water (250 ml) as the ethanol was allowed to evaporate. The cooled solution was treated with 1 N HCl until a precipitate formed (pH 10) which was extracted with methylene chloride (100 ml). The aqueous phase was made strongly acidic with 1N HCl. The thick precipitate was filtered and dried to yield a solid. A portion of this solid (0.65 g) was recrystallised from 50% ethanol (50 ml) to give the title compound as a yellow solid as the hemihydrate; mp slow dec. starting at 260° C.

Analysis for ($C_{20}H_{20}N_4O_4.5H_2O$): C, 61.69; H, 5.44; N, 14.39. Found: C,61.85; H, 5.38; N, 14.45.

EXAMPLE 22

(E)-4-[3-(4-Cyanobenzyl)-1,2,3,6-tetrahydro-1-methyl-2,6-dioxo-9H-purin-8-yl]cinnamic acid.

α-Amino-p-tolunitrile (prepared from α-bromotolunitrile in a modification of the method described by J. H. Short and T. D. Darby, *J. Med. Chem.*, 10 (5), 833, 1967) was treated first with methyl isocyanate followed by cyanoacetic acid according to the method of V. Papesch and E. F. Schroeder (*J. Org. Chem.*, 1951, 16, 1879) to yield 4-[(6-amino-1,2,3,4-tetrahydro-3-methyl-2,4-dioxo-1-pyrimidinyl)methyl]benzonitrile, which was then nitrosated, reduced, and condensed with 4-formylcinnamic acid following an analogous procedure to that of Example 3 to give the title compound as a yellow solid with a melting point greater than 350° C.

Analysis for ($C_{23}H_{17}N_5O_4$): C, 64.63; H, 4.01; N, 16.38. Found: C, 64.58; H, 4.06; N, 16.36.

EXAMPLE 23

(E)-4-[3-(3-Cyanobenzyl)-1,2,3,6-tetrahydro-1-methyl-2,6-dioxo-9H-purin-8-yl]cinnamic acid.

Following an analogous procedure to that of Example 22, the title compound was prepared with a melting point greater than 300° C.

Analysis for ($C_{23}H_{17}N_5O_4$): C, 64.63; H, 4.01; N, 16.38. Found: C, 64.40; H, 4.04N, 16.45.

EXAMPLE (E)-4-[1-(4-Cyanobenzyl)-1,2,3,6-tetrahydro-3-methyl-2,6-dioxo-9H-purin-8-yl]cinnamic acid.

α - Bromo - p - tolunitrile (5.41 g, 27.6 mmol) was added at once with stirring to a solution of 6-amino-1-methyluracil (V. Papesch and E.F. Schroeder. *J. Org. Chem.* (1951), 16, 1879) (3.90 g. 27.6 mmol) in 1:1 ethanol: 1 N sodium hydroxide (56 ml) at 42° C. After 1.75 hours. the mixture was cooled, filtered and washed with water. The resulting solid and second crop obtained by evaporation of the filtrate were combined (5.80 g) and partially purified by silica gel chromatography followed by repeated trituration with 1:2 methanol; ether to give crude 4-[(6-Amino-1,2,3,4-tetrahydro-1-methyl-2,4-dioxo-3-pyrimidinyl)methyl]benzonitrile (0.86 g), indentified by NMR.

To a refluxing solution of this solid (0.17 g, 0.60 mmol) in 2:1:1 $H_2O$: ethanol: glacial acetic acid (12 ml) was added a solution of sodium nitrite (0.063 g, 0.91 mmol) in water (0.5 ml). After refluxing for one minute, the mixture was cooled with stirring, then filtered to give 4-[(6-amino-1,2,3,6-tetrahydro-1-methyl-5-nitroso-2,4-dioxo-3-pyrimidinyl)methyl] benzonitrile as a purple solid (0.17 g, 77%): m.p. 266° (dec.).

Analysis for ($C_{12}H_{11}N_5O_3$): C, 54.74; H, 3.89; N, 24.55. Found: C, 54.80: H, 3.91: N, 24.49.

This intermediate (0.50 g, 1.7 mmol) was reduced to the dianine with ammonium sulfate according to the method of V. Papesch, H. Grove, and E. F. Schroeder, U.S. Pat. No. 2,602,795. The resulting solid (0.47 g) was directly combined with 4-formylcinnamic acid (0.21 g, 1.2 mmol) and refluxed in nitrobenzene (40 ml) for 30 minutes with distillation of nitrobenzene and water formed (total volume 12 ml). The cooled mixture was filtered and washed with ethanol togive the title compound as a pale yellow solid: m.p.>300° C.

Analysis for ($C_{23}H_{17}N_5O_4$. 0.25 $H_2O$): C,63.95; H, 4.05; N, 16.21. Found: C, 64.05; H, 4.09; N, 16.20.

EXAMPLE (E)-4-(1-Benzyl-1,2,3,6-tetrahydro-2,6-dioxo-3-propyl-9H-purin-8-yl)cinnamic acid.

Following an analogous procedure to that of Example 3, the title compound was prepared with a melting point greater than 300° C.

Analysis for ($C_{24}H_{22}N_4O_4$); C, 66.97; H, 5.15; N, 13.02. Found: C, 67.07; H, 5.19; N, 13.02.

EXAMPLE 26

(E)-4-(3-Benzyl-1,2,3,6-tetrahydro-2,6dioxo-1-propyl-9H-purin-8-yl)cinnamic acid.

Following an analogous procedure to that of Example 3, the title compound was prepared with a melting point greater than 300° C.

Analysis for ($C_{24}H_{22}N_4O_4$); C, 66.97; H, 5.15; N, 13.02. Found: C, 66.80; H, 5.16; N, 13.01.

EXAMPLE 27

Cardiac Effects

The ability of (E)-4-(1,2,3,6-tetrahydro-1,3-dimethyl-2,6-dioxo-9H-purin-8-yl)cinnamic acid to inhibit ADO-induced prolongation of the atrio-to-His bundle conduction time and, thus, its potential for the treatment of cardiac disorders, including heart block, was evaluated in isolated perfused guinea-pig heart preparations.

Male and female guinea-pigs were sacrificed by a blow to the head, and their hearts were quickly removed. The heart was then hung on a retro-grade aortic infusion apparatus. Physiological Krebs-Henseleit solution (in mM; sodium chloride, 120.0, potassium chloride, 4.8, calcium chloride, 2.5, magnesium sulfate, 1.2, potassium phosphate, 1.2, pyruvic acid, 2.0 glucose, 5.5, sodium bicarbonate, 25.0, disodium EDTA 0.6, ascorbic acid, 0.3) at pH 7.4, 34.5-35.5° C., gassed with 95% oxygen, 5% nitrogen, was the infusion medium. The right atrial appendage and wall containing the sino-atrial pacemaker was then removed. The pulmonary artery and the mitral valve were cut. The stimulating electrode was placed on the left atrial appendage. Electrodes were appropriately placed to permit recording of the left atrial (LAE) and His-Bundle (HBE) electrograms. Stimulus delay and duration were usually two milliseconds. The voltage was set at two times threshold, or about 6-9 volts. A grass 54 stimulator was used for stimulation.

Pacing was initiated at a rate that ensured one to one capture and later was set to 2-3 Hz. Control atria-His Bundel times (A-H intervals) were obtained once the heart had stabilized. Adenosine infusion (5.0 μm, mixed in Henseleit-Krebs solution) was then begun for a period of five minutes. Atrio-ventricular block frequently occurred at pacing frequencies of 3 Hz, so the pacing in these cases was lowered to a rate where one-to-one conduction was seen. This rate was in the range of 1.5-2.5 Hz. Once the A-H interval had stabilized, a recording for maximum ADO effect was obtained. Infusion of varying doses of antagonist concurrent with the 5 μm ADO infusion was then begun. A Razel A-99 syrine pump was used to infuse the antagonist into the perfusate line. The antagonists were made up in 1.0 mM potassium phosphate buffer, pH 7.4, at a stock concentration of 0.2 mM. Final infusion concentration levels of the antagonists were in a range of 0.20–30.0 μm. The antagonists were infused at a given concentration for three minutes before electrogram recordings were obtained. Two antagonists were evaluated per guinea-pig. A wash period of ten minutes between antagonists was done.

A.V. conduction times were measured form the HBE and LAE. The AH interval was defined as the time between the beginning of the simulus artifact and at the beginning of the His bundle spike, i.e., S-H interval. Measurements were compiled for control (no ADO or antagonist), ADO (no antagonist), and ADO plus antagonist (A—A) concentrations. Differences were then calculated by subtracting the control interval in question. Percentage ADO prolongation inhibition (%INH) was calculated by subtracting the A—A difference from the ADO difference, dividing by ADO difference, and multiplying by 100, thus %INH=(ADO diff.-ant. diff.-)/ADO diff.*100. The Kd(50) was then evaluated by an Eadie-Scatchard plot, where (%INH)/(antagonist conc.) was plotted on the ordinate and %INH on the abscissa. Kd(50) was provided by the negative reciprocal of the slope. The mean Kd(50) for (E)-4-(1,2,3,6-tetrahydro-1,3-dimethyl-2,6-dioxo-9H-purin-8-yl)cinnamic acid for five animals was found to be 0.19μm.

EXAMPLE 28

Injection Formulation

| Ingredient | Amount per Ampoule |
| --- | --- |
| Compound of the Invention | 10.0 mg |
| Buffering Agent, q.s. | — |
| Water, q.s. | 1.0 ml |

The compound of the invention is finely ground and dissolved in the water. The pH is adjusted to the proper value by the buffering agent, and the solution is filtered and sterilised by autoclaving before being sealed under sterile conditions in ampoules.

EXAMPLE 29

Suppository Formulation

| Ingredient | Amount per Ampoule |
| --- | --- |
| Compound of the invention | 75.0 mg |
| Cocoa Butter | 2.0 g |
| or Wecobee ™ Base | |

(Wecobee is a trademark and is a hydrogenated fatty carboxylic acid).

The compound of the invention is finely ground and mixed with the melted Cocoa Butter or Wecobee ™ base. It is then poured into moulds and allowed to cool to afford the suppositories.

EXAMPLE 30

Syrup Formulation

| Ingredient | Amount per 5 ml |
| --- | --- |
| Compound of the Invention | 35.0 mg |
| Ethanol | 2.0 ml |
| Sucrose | 0.5 mg |
| Methylparaben | 0.5 mg |
| Sodium Benzoate | 0.5 mg |
| Cherry Flavour | q.s. |
| Colouring | q.s. |

| Ingredient | Amount per 5 ml |
| --- | --- |
| Water | q.s. to 5.0 ml |

Ethanol, sucrose, sodium benzoate, methylparaben, and flavouring are combined in 70% of the total batch quantity of water. Colouring and the compound of the invention are then dissolved in the remaining water, and finally the two solutions are mixed and clarified by filtration, thus affording a syrup.

EXAMPLE 31

Tablet Formulation

| Ingredient | Amount per Tablet |
| --- | --- |
| Compound of the Invention | 75.0 mg |
| Lactose | 110.0 mg |
| Corn Starch, Pregelatinized | 2.5 mg |
| Potato Starch | 12.0 mg |
| Magnesium stearate | 0.5 mg |

The compound of the invention is finely ground and intimately mixed with the powdered excipients, lactose, corn stach, potato starch and magnesium stearate. The formulation is then compressed to afford tablets.

EXAMPLE 32

Capsule Formulation

| Ingredient | Amount per Capsule |
| --- | --- |
| Compound of the Invention | 75.0 mg |
| Lactose | 400.0 mg |
| Magnesium Stearate | 5.0 mg |

The compound of the invention is finely ground and mixed with the powdered excipients, lactose and magnesium stearate and then packed into two part, gelatin capsules.

Pharmacological Date

Based on studies to date, a positive correlation can be established between the ability of a compound to antagonise adenosine (purine) receptors and its activity in treating or preventing pathophysiological disorders arising from the cell surface effects of adenosine, such as heart block (*Cir. Res.*, 1982, 51, 569 et seq.) and asthma. Accordingly, a representative number of compounds of the present invention were tested for their ability to antagonise the purine receptors using the guinea pig ileum test system.

Procedure

Ilea were removed from sacrificed guinea pigs and placed in organ baths containing oxygenated Krebs-Henseleit buffer. After equilibration, the ilea were stimulated to contract (twitch contraction) using an electrical field-stimulus of 0.1 Hz, 0.5 ms duration and maximal voltage. Under these conditions, the twitch contraction results from the release of acetylcholine.

Concentration response curves to the purine agonist, 2-chloroadenosine, were determined first in the absence and then in the presence of multiple concentrations of the compounds of the invention. One concentration of each compound was used per tissue. Quantification of purine receptor antagonism was accomplished using the Schild regression technique, i.e. plots of log (dose-ratio-1) vs log compound concentration, and the $pA_2$ determined by regression of the data points to the x-intercept, where log (dose-ratio-1) is zero. Since the slopes of these regressions were not different from unity, the $pA_2$ may be considered the pKb, i.e. the negative log of the dissociation constant of the compound for the purine receptors.

Results

The compounds of the invention tested in this way and the results of each test are set forth below.

| Compound of Example No. | $pA_2$ Guinea pig ileum (slope) | Compound of Example No. | $pA_2$ guinea pig ileum (slope) |
|---|---|---|---|
| 6 | 7.7 (0.9) | 15 | 7.1 (0.9) |
| 11 | 7.0 (1.0) | 18 | 7.1 (0.9) |
| 14 | 7.5 (1.0) | 19 | 7.45 (1.0) |
|  |  | THEOPHYLLINE | 4.9 (1.1) |

These results indicate clearly that the compounds of the present invention are capable of antagonizing adenosine receptors and that they are superior in their effect than the prior art adenosine antagonist, theophylline. The compounds of the present invention are, therefore, useful in the treatment or prophylaxis of pathophysiological disorders arising form the cell surface effects of adenosine.

Toxicity Data

The toxicity of a representative number of compounds of the present invention was determined by using the standard $LD_{50}$ test. The compounds were administered intraperitoneally to mice and the results are set forth below.

| Compound of Example No. | $LD_{50}$ (mg/kg) |
|---|---|
| 1 | >500 |
| 6 | >500 |

-continued

| Compound of Example No. | $LD_{50}$ (mg/kg) |
|---|---|
| 10 | >100 |
| 12 | >100 |
| 14 | >100 |
| 16 | >100 |
| 18 | >100 |

The anti-HIV activity of various compounds was tested using an in-vitro assay system as described in H Mitsuya et al; (Proc Natl. Acad.Sci. USA Vol 82 pp 7096-7100, October 1985)

From the information obtained the 50% effectivedose ($ED_{50}$ value) was estimated and the results expressed as active (+) or very active (++). Effects were seen at various concentrations of the drug ranging from $3\mu M$ to $30\mu M$.

| Example | $\mu M$ | $ED_{50}$ |
|---|---|---|
| 14 | 30 | + |
| 25 | 30 | + |
| 26 | 30 | + |
| 15 | 3-15 | ++ |

We claim:
1. A method for the treatment of a virus infection in a virus infected animal which comprises administering to said animal a therapeutically effective amount of the compound
   (E)-4-(1-benzyl-1,2,3,6-tetrahydro-2,6-dioxo-3-butyl-9H-purin-8-yl) cinnamic acid or
   (E)-4-(3-benzyl-1,2,3,6-tetrahydro-2,6-dioxo-1-butyl-9H purin-8-yl) cinnamic acid or a pharmaceutically acceptable salt thereof.
2. A method according to claim 1 wherein said animal is a mammal.
3. A method according to claim 2 wherein said mammal is a human being.
4. A method according to claim 2 wherein said virus infection is a retrovirus infection.
5. A method according to claim 3 wherein said retrovirus infection is an HIV infection.
6. A method according to claim 3 wherein said retrovirus infection is an HTLV-1 infection.

* * * * *